(12) United States Patent
Rosenthal (10) Patent No.: US 8,424,537 B2
(45) Date of Patent: *Apr. 23, 2013

(54) VAPORIZER APPARATUS AND METHODS

(76) Inventor: Joshua Rosenthal, Beverly Hills, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/178,485

(22) Filed: Jul. 7, 2011

(65) Prior Publication Data

US 2011/0259972 A1 Oct. 27, 2011

Related U.S. Application Data

(62) Division of application No. 10/767,303, filed on Jan. 30, 2004, now abandoned.

(51) Int. Cl.
*A24F 1/28* (2006.01)
*A24F 1/10* (2006.01)
*A61L 9/00* (2006.01)
*B01J 7/00* (2006.01)

(52) U.S. Cl.
USPC ............ 131/191; 131/330; 422/305; 422/306

(58) Field of Classification Search .................. 422/305, 422/306; 239/13; 131/191, 194, 330, 273; 128/202.21
See application file for complete search history.

(56) References Cited

U.S. PATENT DOCUMENTS

| 4,141,369 | A | * | 2/1979 | Burruss ........................ 131/330 |
| 5,402,803 | A | * | 4/1995 | Takagi .......................... 131/200 |
| 5,651,942 | A | * | 7/1997 | Christensen .................. 422/125 |
| 7,997,280 | B2 | * | 8/2011 | Rosenthal .................... 131/191 |
| 2002/0074006 | A1 | * | 6/2002 | Gunn ............................ 131/173 |

OTHER PUBLICATIONS

Web screen shot of www.inavap.com via www.archive.org (Dec. 25, 2008 according to Wayback machine). "Vaporpipe" product is shown.
Photo of Inavap "Vaporpipe" product packaging purchased in Dec. 2011. Photo taken in Jan. 2012.
Web screen shot of www.inavap.com via www.archive.org (Dec. 17, 2008 according to Wayback machine).
Web screen shot of www.inavap.com via www.archive.org (Oct. 16, 2008 according to Wayback machine).
Web screen shot of www.inavap.com via www.archive.org (Feb. 12, 2007 according to Wayback machine).

* cited by examiner

*Primary Examiner* — Regina M. Yoo
(74) *Attorney, Agent, or Firm* — George P. White (57) ABSTRACT

A vaporizing device with two concentric tubes for volatizing and inhaling one or more constituents of various vaporizable substances, such as medicines and plant materials. Devices may be successfully operated using the flame from a standard butane cigarette lighter or the like as the sole heat source. Concentric tubes, an inner tube with two open ends and an outer tube with one closed end provide a serpentine pathway for an airflow. An additional embodiment of the device provides a substitute for a standard slider-bowl allowing for the conversion of a standard water pipe into a vaporizing device. Other embodiments allow for vaporization of cigarettes.

8 Claims, 9 Drawing Sheets

VAPORIZER APPARATUS AND METHODS

RELATED APPLICATIONS

This application is a divisional application of U.S. application Ser. No. 10/767,303 filed on Jan. 30, 2004 and published as U.S.2005/0169814 A1, now abandoned, directed to the non-elected species III. The present application is with application Ser. No. 11/866,224 filed Oct. 2, 2007 and published as U.S.2008/0023003 A1, a continuation-in-part of application Ser. No. 10/767,303. Application Ser. No. 10/767,303 is hereby incorporated by reference in its entirety.

FIELD

This invention relates to the field of heat vaporization of various substances, such as plant substances and medicine to produce inhalable vapors.

BACKGROUND

Vaporization of volatile constituents of various substances without combustion by the application of heat for the purpose of inhaling volatile constituents is a process that has been known. Some have made use of heated stones, heated metal or coals in an isolated chamber. The conduction of heat from such a chamber has been used to release volatile constituents from medicinal substances in an adjacent chamber in order to make possible inhalation of the volatile constituents.

Some use heat from electrical heating elements as a means to accomplish vaporization without significant combustion. Other devices use the application of heat from a flame through an intermediary barrier of glass, metal, or other heat conducting material, thereby preventing direct contact of the flame with the substance to be vaporized. Still other devices rely on the transfer of heat from the combustion of a solid fuel source, generally a carbonaceous material. Then there are a number of devices that rely on the application of internally or externally produced hot air to a vaporizable substance in order to achieve vaporization.

An advantage of vaporization of a substance over combustion of that same substance can be the elimination of unwanted combustion byproducts and therefore a reduction in the health risks associated with inhalation. Overall, past devices can present effective means of releasing various volatile constituents from substances while avoiding the commingling of said volatile constituents with unwanted combustion by-products. Although they may effectively vaporize vaporizable substances, many of the devices referred to above also have disadvantages including the user inhaling unwanted substances.

SUMMARY

The present teaching involves a vaporizer that can comprise an inner vessel and an outer vessel. The inner vessel can be open at both ends, and can have a partition spanning its interior cross-sectional area separating the inner volume of the inner vessel into a vaporization chamber and a drawing chamber. This partition can have screening holes through it allowing vapors to pass from the vaporization chamber into the drawing chamber.

When the inner vessel is inserted into the outer vessel, a device can be created with a particular air path. Depending upon the specific embodiment, air is able to pass from the space between the inner and outer vessels into the vaporization chamber in the inner vessel.

In some versions, a vaporizing device can replace the standard slider-bowls used in many water pipes allowing the water pipe to be converted into a vaporizing device. In other variations, a device can be in a version capable of vaporizing items of a cigarette form-factor.

DETAILED DESCRIPTION

General Description of a Class of Embodiments

In one aspect, the present invention teaches a class of embodiments that are portable vaporizing devices, the devices generally comprising an outer vessel and an inner vessel held together by a fastener. Some versions also comprise an outer insulating wrap.

The outer vessel has a closed distal end and an open proximal end. The inner vessel has an open proximal end as well as an open distal end. The inner vessel also has a partition within it, spanning the inner cross-sectional area of the vessel. The partition divides the inner volume of the inner vessel into two chambers, a vaporization chamber distally and a drawing chamber proximally. The partition also has screening holes through it to allow air to be drawn from the vaporization chamber through the partition into the drawing chamber, while keeping the vaporizable substance in place inside the vaporization chamber, the partition thus functioning essentially as a screening mechanism.

When this first example device is assembled, the inner vessel is inserted into the outer vessel through the open proximal end of the outer vessel such that the distal end of the inner vessel is made to abut the inside surface of the distal end of the outer vessel while the proximal end of the inner vessel still protrudes from the opening at the proximal end of the outer vessel. The distal end of the inner vessel preferably abuts the inside of the closed distal end of the outer vessel, substantially closing off the opening at the distal end of the vaporization chamber, thus substantially trapping the vaporizable substance in the vaporization chamber.

In some versions, the assembly may be designed so as to direct air to pass into the vaporization chamber by allowing it to travel around the distal end of the inner vessel through intentionally unsealed gaps between the distal end of the inner vessel and the inner surface of the closed distal end of the outer vessel, and then on into the vaporization chamber. As a second version, the design may be to make air inlet openings through the surface of the inner vessel near the distal end of the vaporization chamber to allow air to pass from the space between the inner vessel and the outer vessel through these openings into the vaporization chamber. A third version is a combination of gaps at the abutment area and openings through the surface of the vaporization chamber.

The fastener holds the two vessels together in this abutted position. The inner vessel therefore must be of such girth that it can be readily inserted and removed through the open proximal end of the outer vessel. The inner vessel should be longer than the outer vessel so that when fully inserted into the outer vessel, the proximal end of the inner vessel protrudes beyond the open proximal end of the outer vessel.

Numerous alternative possible embodiments and versions will work satisfactorily. The exact dimensions of the vessels and fastener specified are not critical to the proper functioning of the vaporizer so long as the parts fit each other. A somewhat larger or smaller vessel assembly as regards length and/or 115 circumference is possible so long as there is an appropriate air space between the outer surface of the inner vessel and the inner surface of the outer vessel to permit proper airflow through the device during usage.

The vessel surfaces may be made thinner or thicker in places so long as they are:
1) sufficiently thick to withstand the applied heat, the hot air flow through the device, and the repeated surface-to-surface contact involved in assembling and disassembling the device; and
2) sufficiently thin to allow ready conduction of heat from a flame through the surface of the outer vessel to the air in-between the two vessels.

A further consideration in many embodiments is to make sure that the user's hand will not be burned once heat is applied to the distal end of the outer vessel and so there must be sufficient distance between the spot where the heat is applied and the area where the hand holds the device, so as to eliminate conduction of unacceptable levels of heat to the area where the hand holds the device. The characteristics of the materials used for construction will thus have impact on the acceptable dimensions of the constructed device. Similar considerations must be kept in mind in some embodiments to ensure that the vessel lengths are sufficiently long to prevent excessive heat being conducted to the proximal end of the inner vessel so that a user's lips are not burned. A shorter vessel assembly may be acceptable if an insulating wrap is wrapped around the outer vessel proximal to the heating area, thus preventing the hand from being burned by heat conduction through the outer vessel so long as the device still has sufficient length to prevent overheating of the proximal end of the inner vessel. The wrap can be made of any heat insulating substance such as rubber, KEVLAR® brand sheet material, leather, fabric, or the like.

A partition in the inner vessel may be placed at different positions to create a larger or smaller vaporization chamber size to accommodate larger or smaller amounts of vaporizable substance as desired. Further, the pattern and/or shape of screening holes through a partition can be varied in numerous ways without problem. For example, the screening holes could be round, slotted, diamond-shaped or any other shapes. There are any number of screening hole patterns which could effectively function as a screening mechanism to allow vapors to pass and prevent solid un-vaporized substance from being inhaled. The number, shape and size of screening holes selected will affect the drawing pressure necessary to produce a given airflow through the device.

Another necessary feature of the many embodiments is that there be one or more air intake vents located away from the heating area, preferably near the proximal end of the outer vessel. These vents are for the purpose of clean air intake into the space between the inside surface of the outer vessel and the outside surface 155 of the inner vessel. Again, the number of air intake vents, their exact size and their exact placement is not critical to the proper functioning of the unit. However, placing these vents away from the heating area is a key feature of this invention as it serves the important purpose of separating the air intake into the device from the area where fuel combustion occurs externally, thus minimizing the inhalation of fuel exhaust fumes into the device and into the lungs.

The space between the opening in the proximal end of the outer vessel and the outer surface of the inner vessel can serve as an air intake vent or, alternatively, openings of various designs can be made through the surface of the outer vessel to serve as air intake vents. The air intake vents can be placed in any number of patterns, using a smaller or larger number of vents, as well as a somewhat smaller or larger vent size, or even different shaped vents. The number and size of the vents chosen will also affect the drawing pressure necessary to produce a given airflow through the device.

A fastener should be such that it holds the inner and outer vessels in position relatively firmly once they are assembled together. A fastener should also be such that it is easily releasable for ready disassembly and reloading of the device. There are many possibilities that will function successfully for the present application.

One possibility is a grommet, preferably made of elastic material, such as rubber, which encircles the outer surface of the inner vessel at the appropriate region and provides a seal at the mouth of the opening of the outer vessel when the inner vessel is fully inserted into the outer vessel. A properly fitted fastener of this type can serve to fasten the two vessels together and can also be readily unfastenable, thus functioning essentially as a removable locking one-holed stopper. When such a fastener is used, the space between the open proximal end of the outer vessel and the outer surface of the inner vessel can no longer be used as a vent since that area is sealed. One option would be to make vent openings through the surface of the outer vessel as discussed above. A second option for air intake vents in this case is to make openings through the fastener although, depending upon the design, such openings might collapse e.g. if the fastener is made of an elastic material.

Other possibilities for fasteners would be to use a channel-locking or screwing mechanism to hold the two vessels together. The surfaces of the two vessels can be fitted with, or designed to include, outcroppings or threads of various types that interlock to hold the two vessels in place once the inner vessel is inserted into the outer vessel and twisted, for example. In such an arrangement, the locking mechanism itself can have air intake vents, which pass through it to allow proper airflow through the device, or alternatively, the air intake vents can be made through the surface of the outer vessel away from the heating area as above. Depending upon which materials are used to fabricate the vessels, these channel locking and screwing embodiments have the drawback of being potentially more expensive to produce due to the more complex work involved.

Any number of reusable fasteners could work successfully to hold the inner and outer vessels together when assembled and then to allow easy disassembly for reloading. The human hand can function as the necessary fastener to hold the two vessels in position during use although this solution has obvious inconveniences. Still other fasteners, e.g. an O-ring, rubber band, or strap, may be employed.

To function properly, it can be important that sufficient air can flow into the vaporization chamber from the space between the inner surface of the outer vessel and the outer surface of the inner vessel. One method of allowing this airflow is to create gaps at the abutment area where the distal end of the inner vessel abuts the inner surface of the distal end of the outer vessel. For example, depending on the design of the outer vessel, one or more notches around the circumference of the opening at the distal end of the inner vessel can allow airflow into the distal end of the vaporization chamber. A second method to ensure adequate airflow from the space between the two vessels into the vaporization chamber is to make air inlet openings through the surface of the inner vessel into the vaporization chamber.

A number of materials are suitable for constructing the vessels of the present invention. High temperature glass, for example PYREX® brand borosilicate glass, has the advantages of being transparent, being effective at substantially containing heat in the heating area, and of not negatively affecting the taste of the vapors produced. Using, for example, metal, one would lose all or some of these advantages but gain the advantage of making the assembly more durable. Ceramic is another possibility. Other materials or combinations of materials, e.g. metal bonded to glass, could be employed as well. As long as one uses a heat-safe, non-toxic material, which suitably conducts heat to the air, which flows inside the assembly, some degree of success with vaporization should be possible although there is some variation in the exact qualities of the process depending on which materials are chosen.

First Specific Embodiment

Figure 1:
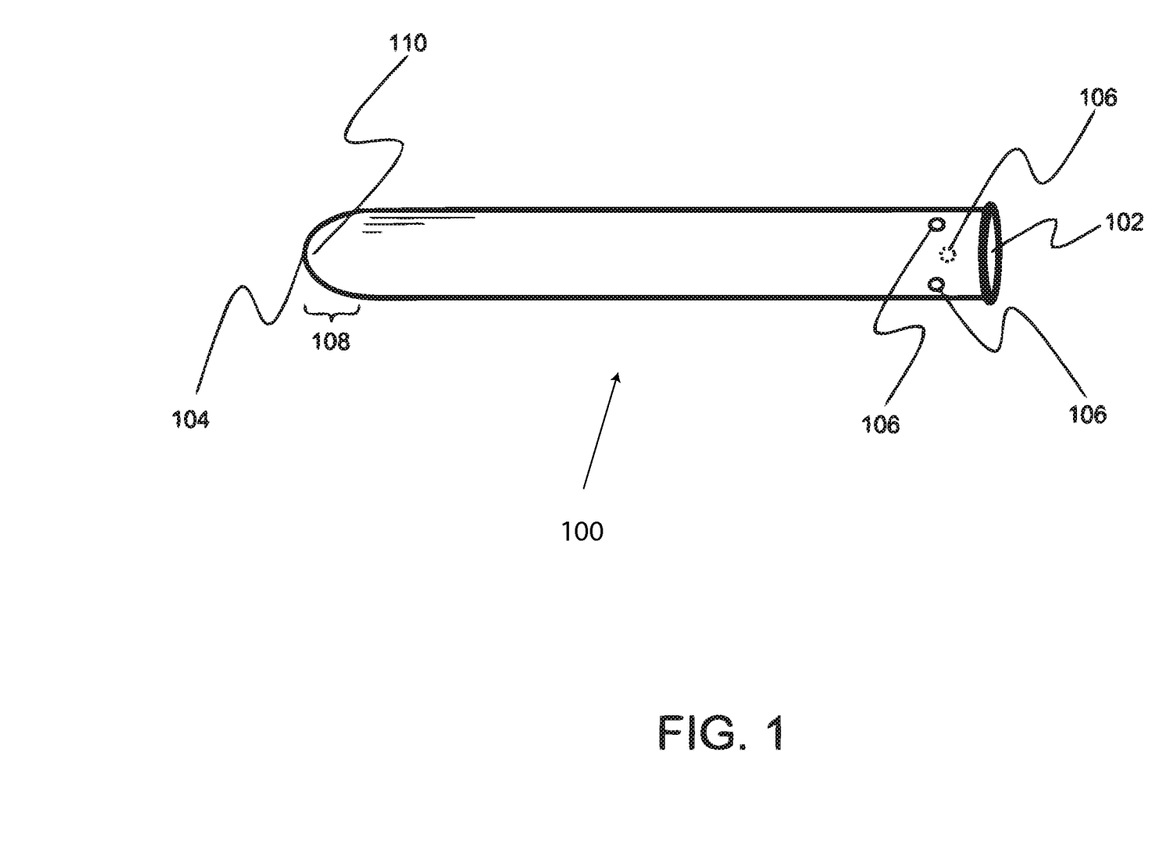
FIG. 1 shows an example of an outer vessel for a vaporizer.

Referring to FIG. 1, there is shown a first specific embodiment of an outer vessel (100). In this embodiment of the invention, the outer vessel (100) is a standard test tube shape, a 15.3 cm long test tube made of high temperature glass, for example, PYREX®, with an open proximal end (102) and a rounded closed distal end (104). Throughout the body of the tube (100) the outer diameter is 19 mm, the inner diameter is 16.6 mm, and the thickness of the glass is 1.2 mm. The open proximal end of the tube (102) flares out slightly, giving it an outside diameter of 20 mm. There is a heavier bead of glass at the closed distal end (104) as well as at the open proximal end (102) of the tube, making the glass approximately 2 mm thick in these areas. Centered 2 cm from the open proximal end (102) of the tube, there are three 5 mm diameter round air intake vents (106) going straight from the outer surface to the inside surface of the tube, the air intake vents (106) being spaced 235 equidistantly around the circumference of the test tube. The most effective heating area (108) is located at the very distal end of the tube and extends approximately 1-2 cm from the end of the tube. The measurements given above are typical. Generally, useful ranges for measurements for outer vessels are from 9 cm to 200 cm in length and diameters ranging from 5 mm to 25 cm. The higher ends of these ranges as well as the extreme low ends of these ranges are probably more valuable for novelty applications as opposed to convenience, but can still yield functional devices. While these ranges are generally preferred for most uses, the device can be made in any size and the invention is not meant to be limited to any particular size or sizes.

Figure 2:
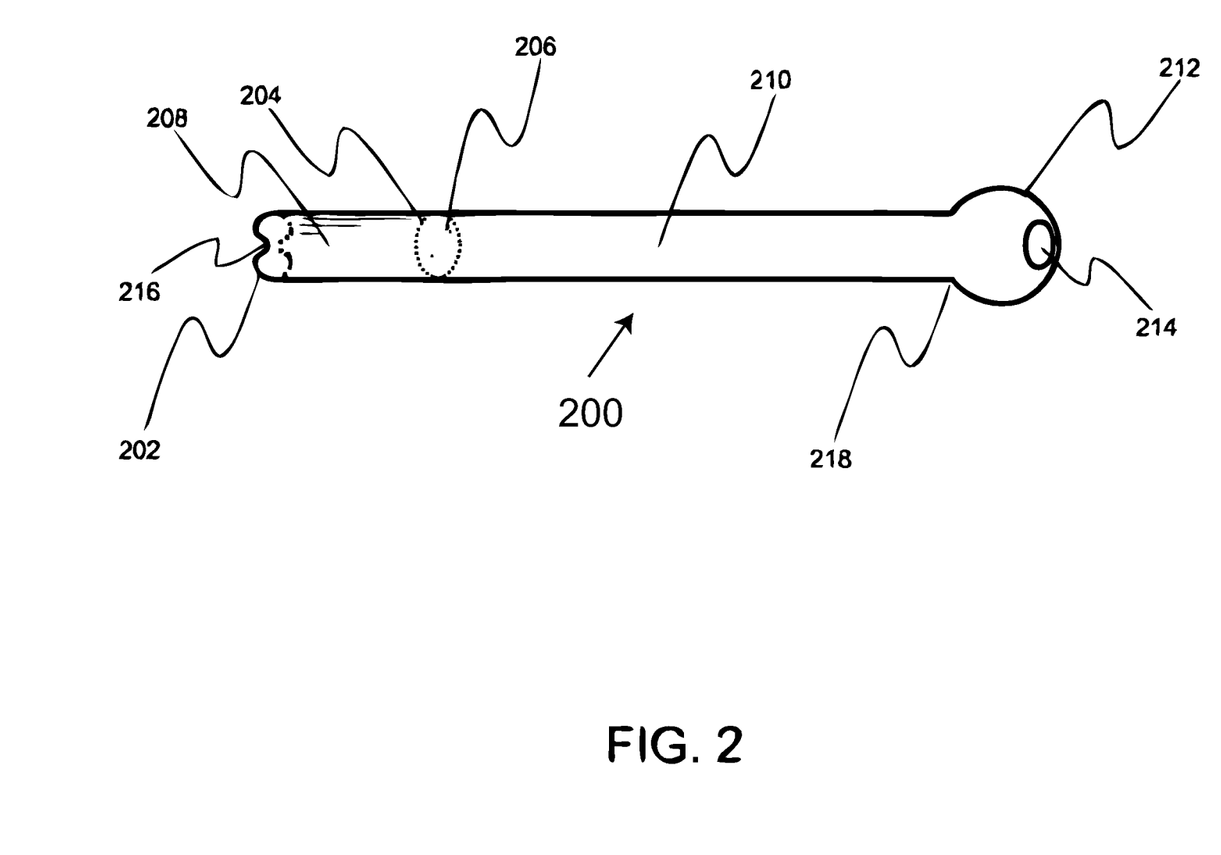
FIG. 2 shows an example of an inner vessel for a vaporizer.

Referring to FIG. 2, there is shown an embodiment of the inner vessel (200). Here, the inner vessel (200) is approximately 17.3 cm long, a high temperature glass tube, straight throughout most of its length, with an open proximal end (214) and an open distal end (202). The outer diameter of the tube (200) is 12 mm and the inner diameter is 10 mm, the thickness of the glass being 1 mm throughout the body of the tube (200). At a distance of 3 cm from the distal end of the tube (202), there is a glass partition (204), 2 mm thick, perpendicular to the walls of the tube (200) spanning the inner cross-section of the tube (200). This partition (204) has through it five screening holes (206), 1.5 mm in diameter each, four placed in a square pattern, the fifth in the center, all spaced approximately equally over the surface of the partition (204). The partition (204) divides the interior space of the inner tube (200) into a vaporization chamber (208) distally and a drawing chamber (210) proximally.

The proximal end of the tube flares out into a spherical mouthpiece (212) extending from the proximal end of the tube (214), distally to 2 cm away from the proximal end of the tube (218). This spherical mouthpiece (212) is 2 cm in diameter and has a surface thickness of approximately 2 mm. On its distal side (218), it has a circular opening to the drawing chamber (210) and at its opposite, most proximal end, it has a 6 mm diameter round opening (214). The openings at both ends of the tube (202) (214) have heavier beads of glass, giving them a thickness of approximately 1.4 mm. The final 1 cm of length of the distal end of the inner tube is crimped together to form two inwardly facing crests 180 degrees around the circumference from one another, such that the two crests close to a distance of 4 mm apart at their closest point to one another (216). This crimp (216) allows for better airflow between the distal end of the inner tube (202) and the inner surface of the distal end of the outer tube (104) on into the vaporization chamber (208). The measurements given above are typical. Generally, useful ranges for measurements for inner vessels are from 9 cm to 200 cm in length and diameters ranging from 2 mm to 25 cm. The higher ends of these ranges as well as the extreme low ends of these ranges are probably more valuable for novelty applications as opposed to convenience, but can still yield functional devices. While these ranges are generally preferred for most uses, the device can be made in any size and the invention is not meant to be limited to any particular size or sizes.

A heavier bead of glass is used on the distal end of the inner (202) and outer (104) tubes. Beyond serving to protect the heating area (108) from breakage due to applied heat, this heavier bead functions to prevent contact breakage in these areas that make solid on solid contact with one another during usage.

Figure 3:
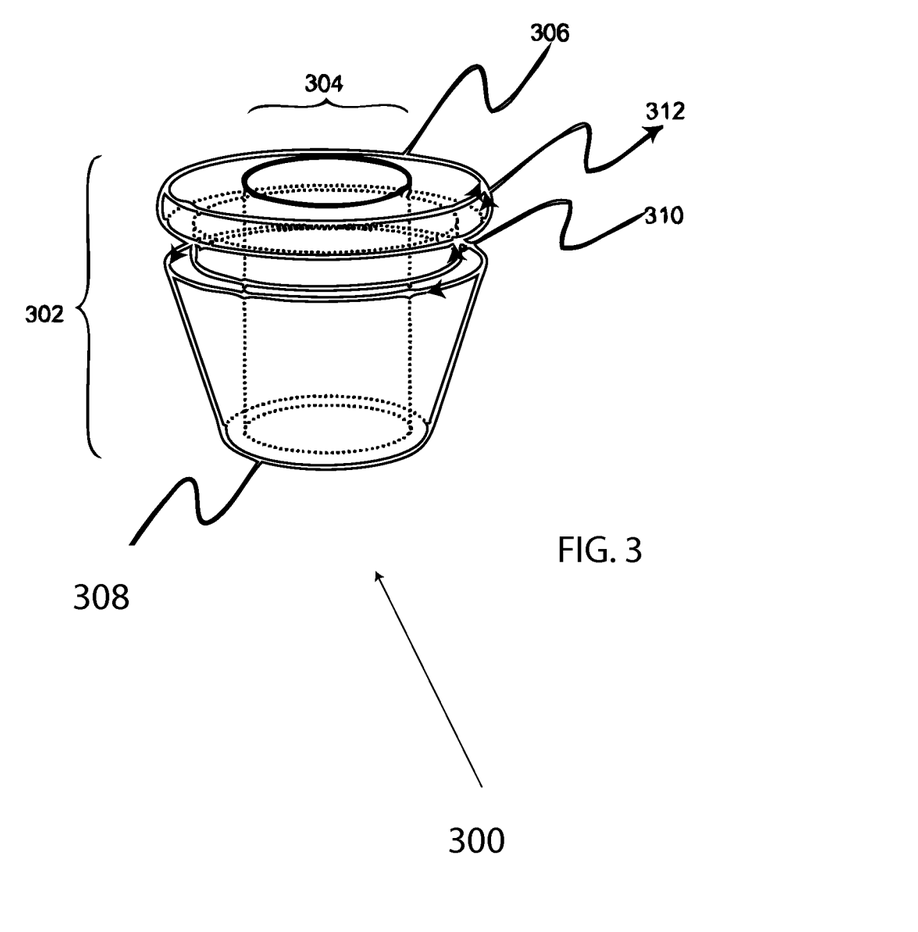
FIG. 3 shows an example of a grommet.

Referring to FIG. 3, there is shown an embodiment of a fastener (300). In this embodiment, the fastener is a grommet (300), preferably made from rubber or other elastic material. The grommet (300) is essentially a short sleeve or wide ring, designed to function as a removable locking one-holed stopper. It measures 13.8 mm from end to end along its cylindrical length (302). It has an inner diameter (304) of 9.2 mm throughout its length (302) and an outer diameter that ranges from 15.5 mm at its proximal end (306) to 12.2 mm at its distal end (308), the thickness of the ring varying along the length (302).

Beginning at the distal end of the grommet (308), where the outer diameter is 12.2 mm, and moving proximally along the grommet (300), the material thickens steadily until 8 mm along the grommet (300), where the outer diameter is 13.8 mm. At this point, there is a groove (310) 2.6 mm wide around the circumference of the grommet (300), where the outer diameter is 12.2 mm. Then the final 3.2 mm in length (302) constitutes a rounded lip (312) where the outer diameter is 15.5 mm at its widest point. The measurements given above are typical. Generally, useful ranges for measurements of grommets (300) are from 5 mm to 20 cm in length and diameters ranging from 5 mm to 25 cm. The higher ends of these ranges as well as the extreme low ends of these ranges are probably more valuable for novelty applications as opposed to convenience, but can still yield functional devices. While these ranges are generally preferred for most uses, the device can be made in any size and the invention is not meant to be limited to any particular size or sizes. Of course, the particular sizes of grommet (300) to fit particular embodiments will be dependent on the sizes of the vessels (100) (200) and so must be chosen based on the measurements of the vessels (100) (200).

Use of a rubber grommet (300) as a fastener has some distinct advantages. If a rubber grommet wears out, it is easily and inexpensively replaced. Further, the rubber grommet serves as a shock absorbing mechanism to minimize glass on glass impact.

Figure 4:
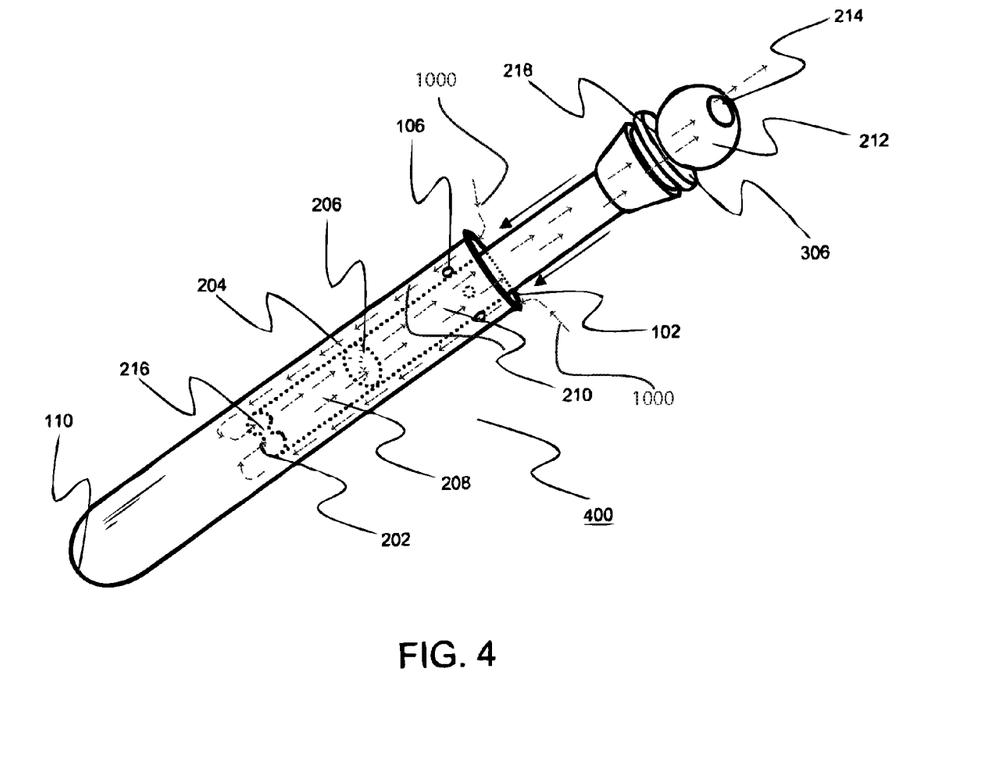
FIG. 4 shows an example of an assembled vaporizer, including an airflow path.

Referring to FIG. 4, there is shown an embodiment of a portable vaporizing device (400). The portable vaporizing device (400) is assembled by first sliding the grommet (300) onto the distal end of the inner tube (202) along the length of the tube (200) so that the proximal (wide) end (306) of the grommet (300) is brought to abut the distal end of the spherical mouthpiece (218), located at the proximal end of the inner tube (200). This grommet (300)/inner tube (200) assembly is then inserted into the outer tube (100) such that the distal end (202) of the inner tube is brought to abut the inside of the closed distal end (402) of the outer tube (100). In this position, the grommet (300) fits into place in the opening (102) of the open proximal end of the outer tube to provide removable locking seal at the opening in the proximal end of the outer tube. This configuration inherently provides for the airflow path 1000 as diagramed in FIG. 4. When suction is applied at the mouthpiece opening (214), external ambient air is drawn in at the air vent formed by the space between the inner tube (200) and outer tube (100). The airflow follows a path between the two concentric tubes until it reaches the distal open end of the inner tube (216). Due to this construction and arrangement of the tubes, the airflow continues into the distal end of the inner tube and through the vaporization region (208). Now transporting the vaporization product, the airflow continues through the inside of the inner tube up to the mouthpiece for a user to inhale. As is seen in FIG. 4, the airflow starts at the intake vent that is sufficiently distant from the heat source as to not contain a substantial amount of combustion by-product, unburned chemicals from the fuel of the flame or other noxious fumes.

Figure 8A:
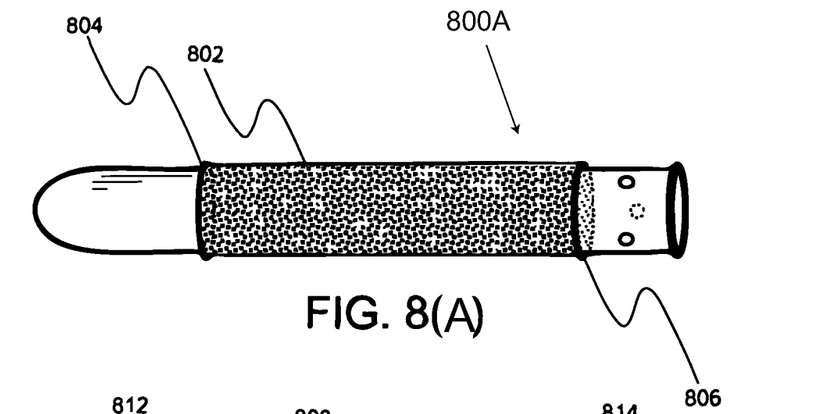
FIG. 8A shows a wrap that does not extend over the air intake vents.
Figure 8B:
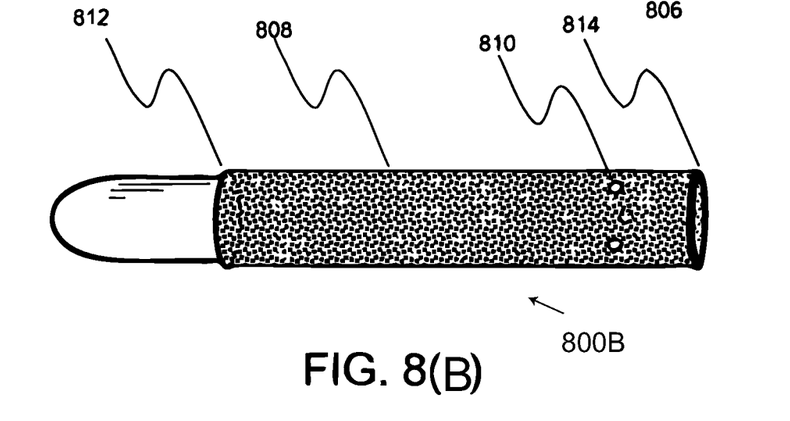
FIG. 8B shows a wrap that extends over the air intake vents.

Referring to FIGS. 8A and 8B, two embodiments of an optional outer wrap on an outer vessel (800A) (800B) are shown. The wrap (802) (808) may be made of rubber, leather, or other insulating material, such as KEVLAR® brand fabric sheet material, and is to be wrapped around the outer vessel (100) proximal to the heating area (108) so as to protect a user's hand from burns should the outer vessel (100) become too hot. The wrap (802) (808) also serves to remind a user of the acceptable areas to hold the device (400) during and after use. The wrap (802) can extend from just distal of the air intake vents (106) near the proximal end of the outer vessel (102) along the outer surface of the outer vessel (100) until about 4 cm from the distal end of the vessel (104), so as not to cover the heating area (108). Alternatively, the wrap (808) can extend all the way to the proximal end of the outer vessel (102), with holes made through the wrap (810) corresponding to the position of the air intake vents (106), thus not obstructing air intake into the device through the air intake vents (106).

If an optional external insulating wrap (802) (808) is to be used, another option would be to place extra raised ridges of material around the circumference of the outer surface of the outer vessel (100) to prevent the wrap from sliding out of proper position. Where the wrap (802) extends from proximal of the heating area (108) until just distal of the air intake vents (106), two raised ridges of material can be used, one ridge (804) at approximately 4 cm from the distal end of the outer vessel and a second raised ridge (806) of material around the circumference of the outer surface of the outer tube (100) just distal to the positioning of the air intake vents (106). When tightly wrapped, these ridges (804) (806) of material would then serve to keep the outer wrap (802) in proper position, preventing the outer wrap (802) from sliding into the heating area (108) of the outer vessel or covering the air intake vents (106).

Where the wrap (808) is designed to extend all the way to the proximal end of the outer vessel (102), one raised ridge (812) would be placed at approximately 4 cm from the distal end of the outer vessel (104) while the heavier bead of glass at the proximal end of the vessel (814) will serve as the second ridge to hold the wrap in place. The measurements given above are typical. Depending on the dimensions of a particular embodiment of the invention, the wrap may vary in size significantly. The measurements above are given to illustrate a wrap that would properly fit the example of the 'portable vaporizer embodiment' (400) given. The vaporizing device and the wraps to fit it can be made in any size and the invention is not meant to be limited to any particular size or sizes.

Second and Third Specific Embodiments

Figure 6A:
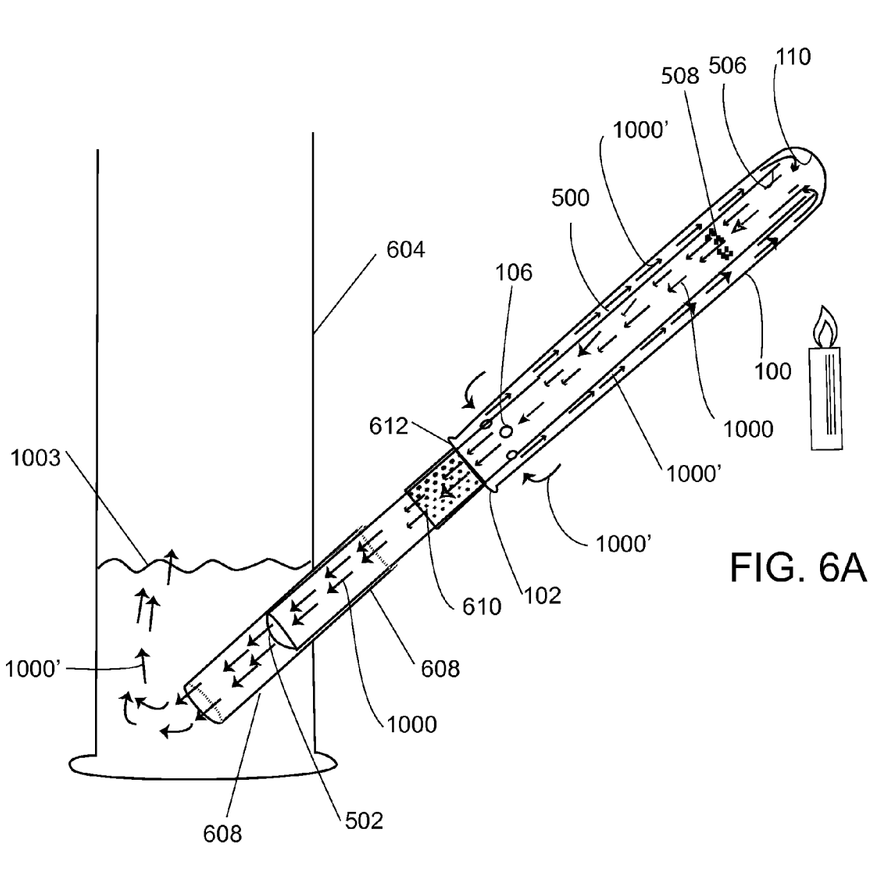
FIG. 6A shows an example of an assembled slider-bowl replacement embodiment, including an airflow path.

Two additional embodiments of the device are also disclosed, which are designated the 'slider-bowl replacement embodiment' (600) as shown in FIG. 6, and the 'cigarette holder embodiment.'

The 'slider-bowl replacement embodiment' (600) is designed to replace a standard slider-bowl so as to provide a means for vaporization in conjunction with commonly manufactured water pipes (610).

Figure 5:
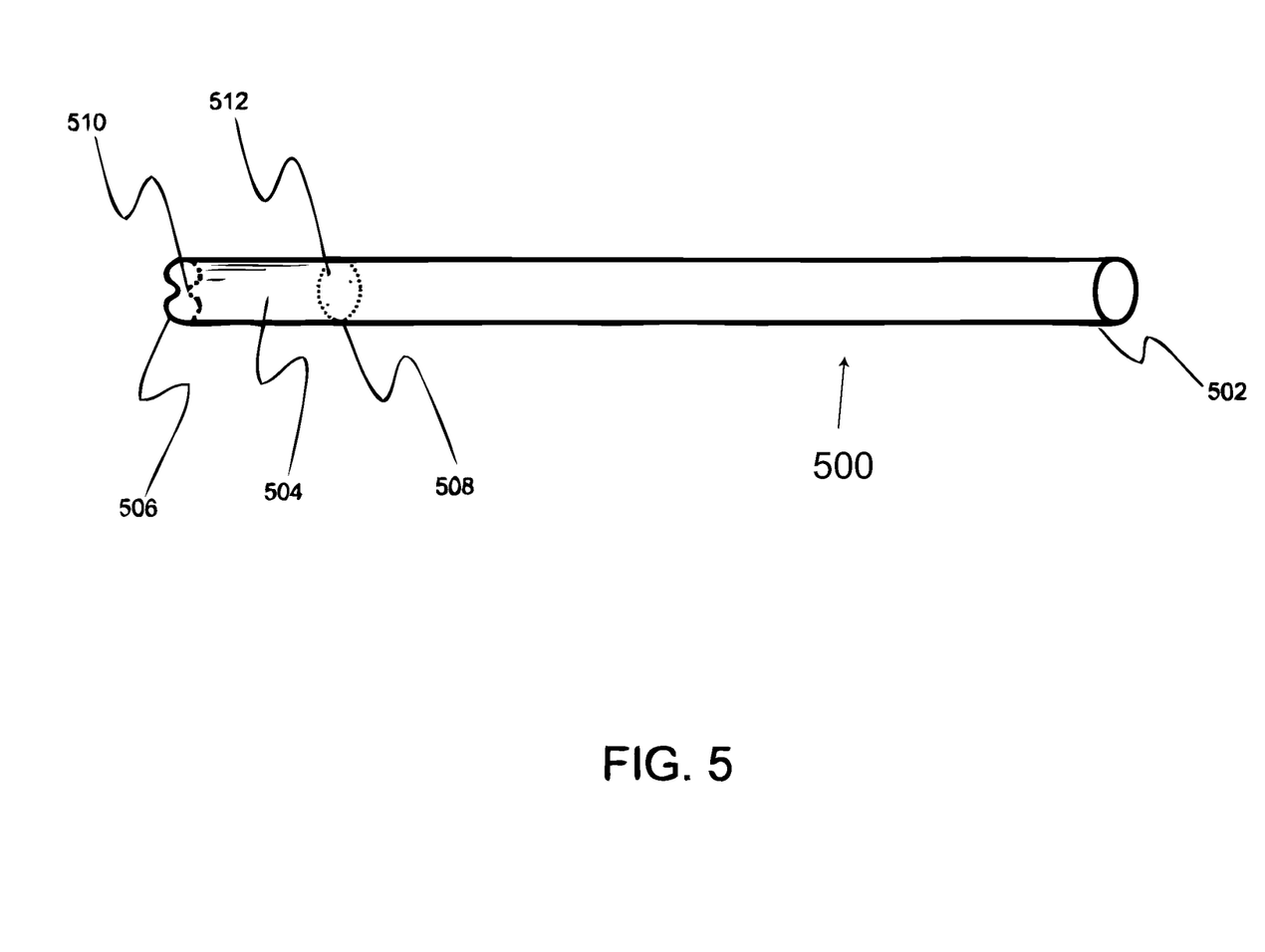
FIG. 5 shows an example of an inner vessel for a slider-bowl replacement embodiment version.

Referring to FIG. 5, an example of an inner vessel (500) for the 'slider-bowl replacement embodiment' is shown. This inner vessel (500) is a tube made proportionally longer than the one utilized for the 'portable vaporizer embodiment' (200). There is no spherical mouthpiece (212) at the proximal end of the inner vessel (502) as there was in the portable vaporizer example (200). Instead, the proximal end of the inner vessel (502) is designed to be inserted into the slider-bowl receiving tube of a water pipe (608).

Referring to FIG. 6, an example of an assembled 'slider-bowl replacement embodiment' (600) is shown. The outer vessel (100) is substantially the same as the outer tube from the 'portable vaporizer embodiment' (100) above. This example of the 'slider-bowl replacement' embodiment (600) utilizes an outer tube (100) with a length of 15.3 cm, an outer diameter of 19 mm and an inner diameter of 16.6 mm, as in the 'portable vaporizer embodiment' (400) above. The inner tube (500) has a constant outer diameter of 12 mm along its entire length and is 21.5 cm long. The distal end of the inner tube (506) has the same crimping (510) as in the 'portable vaporizer' example (400) above and the partition (508) is likewise placed at 3 cm from the distal end (506) of the inner tube. The screening holes (512) are substantially the same as in the 'portable vaporizer embodiment' (400) above. The measurements given above are typical. Generally, useful ranges for measurements for outer vessels for the 'slider-bowl replacement' embodiment are from 4 cm to 75 cm in length and diameters ranging from 5 mm to 25 cm. Generally, useful ranges for measurements for inner vessels for this embodiment are from 4 cm to 75 cm in length and diameters ranging from 2 mm to 25 cm. The higher ends of these ranges as well as the extreme low ends of these ranges are probably more valuable for novelty applications as opposed to convenience, but can still yield functional devices. While these ranges are generally preferred for most uses, the device can be made in any size and the invention is not meant to be limited to any particular size or sizes. This configuration inherently provides for the airflow path 1000' as diagramed in FIG. 6A.

When suction is applied to the water pipe (only partially shown), the air pressure in the main chamber is reduced. This, in turn reduces air pressure at the proximal end of the inner tube (500), ultimately causing external ambient air to be drawn in at the air vent formed by the space between the inner tube and outer tube (100). The airflow follows a path between the two concentric tubes until it reaches the distal open end (506) of the inner tube. Again, due to the construction and arrangement of the tubes, the airflow continues into the distal end of the inner tube and through the vaporization region. The air is heated by a flame or other source to the point that it can vaporize the volatile portion of the material in the vaporization chamber. Now transporting the vaporization product, the airflow continues through the inside of the inner tube to the slider-bowl receiving tube (608) of the water pipe (604) and into and through the water and up past the water line 1003 in the main clamber for a user to inhale. This airflow starts at the intake vent that is sufficiently distant from the heat source as to not substantially contain unburned chemicals from the fuel of the flame or other noxious fumes from the heat source.

In this example of the 'slider-bowl replacement embodiment,' (600) the grommet (300) is replaced with a short sleeve of tubing (602), preferably made of an elastic material, such as rubber. If an elastic sleeve (602) is used, it will have an inner diameter of 10.5 mm, a length of approximately 1.3 cm, and a thickness of approximately 3 mm. This diameter allows the sleeve when stretched to fit snugly onto the inner tube. The sleeve (602) is slid onto the inner tube (500) such that its distal end (612) is at 14.4 cm from the distal end of the inner tube (506). In this embodiment, the weight of the outer tube (100) substantially creates a seal at the open proximal end of the outer tube (102) as it rests on the distal end of the sleeve (612) and is held there by gravity. The proximal end of the sleeve (610) abuts the mouth (606) of the slider-bowl receiving tube where the mouth (606) of the slider-bowl receiving tube circles the inserted inner tube (500), substantially creating a seal at this location as well as limiting how far the inner tube (500) can slide into the slider-bowl receiving tube (608) which is also known as a downstem.

If an elastic ring(s) (not pictured) is used, it will have an inner diameter of approximately 10.5 mm, slightly less than the 12 mm outer diameter of the inner tube (500) so it will fit snugly when stretched, and a ring thickness of approximately 3 mm. A single ring may be utilized in the same manner as the sleeve above, where the ring is placed so its distal side abuts and substantially seals the open proximal end of the outer tube (102) and its proximal side abuts and substantially seals the mouth of the slider-bowl receiving tube (606) when the device is assembled. Alternatively, two rings (not pictured) may be utilized, one ring positioned so its distal side abuts and substantially seals the open proximal end of the outer tube (102) and the second ring positioned so its proximal side abuts and simultaneously substantially seals the area where the mouth (606) of the slider-bowl receiving tube circles the inserted inner tube (500). Yet another viable alternative is to utilize only a single ring and position it to abut only the open proximal end of the outer tube (102) substantially creating a seal at this juncture as well as providing a support on which the inner tube can rest in proper position. Likewise, a single ring can be utilized and positioned so as to only abut the mouth of the slider-bowl receiving tube (606) where it circles the inserted inner tube (500) providing a seal at this juncture as well as stopping the inner tube (500) from sliding too far into the slider-bowl receiving tube (608).

An advantage of using a sleeve (602) or ring(s) (not pictured) as opposed to a grommet (300) in this embodiment is that the outer tube (100) can simply be lifted off easily for reloading, etc., rather than having to be released from the stronger seal created by the grommet (300) in the portable vaporizer embodiment (400). The dimensions of rings or sleeves that are useful depends upon the dimensions of the tubes chosen as the ring(s) or sleeve preferably fits snugly around the outside surface of the inner vessel (500), and is thick enough that the open proximal end of the outer vessel may rest upon it as well as thick enough to create the above-mentioned seals at the appropriate junctures. However, the device can be made in any size and the invention is not meant to be limited to any particular size or sizes.

Currently, most standard slider-bowls have tubes with an outside diameter of 12, 15 or 16 mm and therefore most standard slider-bowl receiving tubes (608) are made to receive slider-bowl tubes with one of these outer diameters. Therefore, in this example, using an inner tube (500) with a fixed outside diameter along its length of 12 mm will allow the proximal end of the inner tube (502) to fit properly into the smallest of the three standard sizes of slider-bowl receiving tubes (608).

Figure 6B:
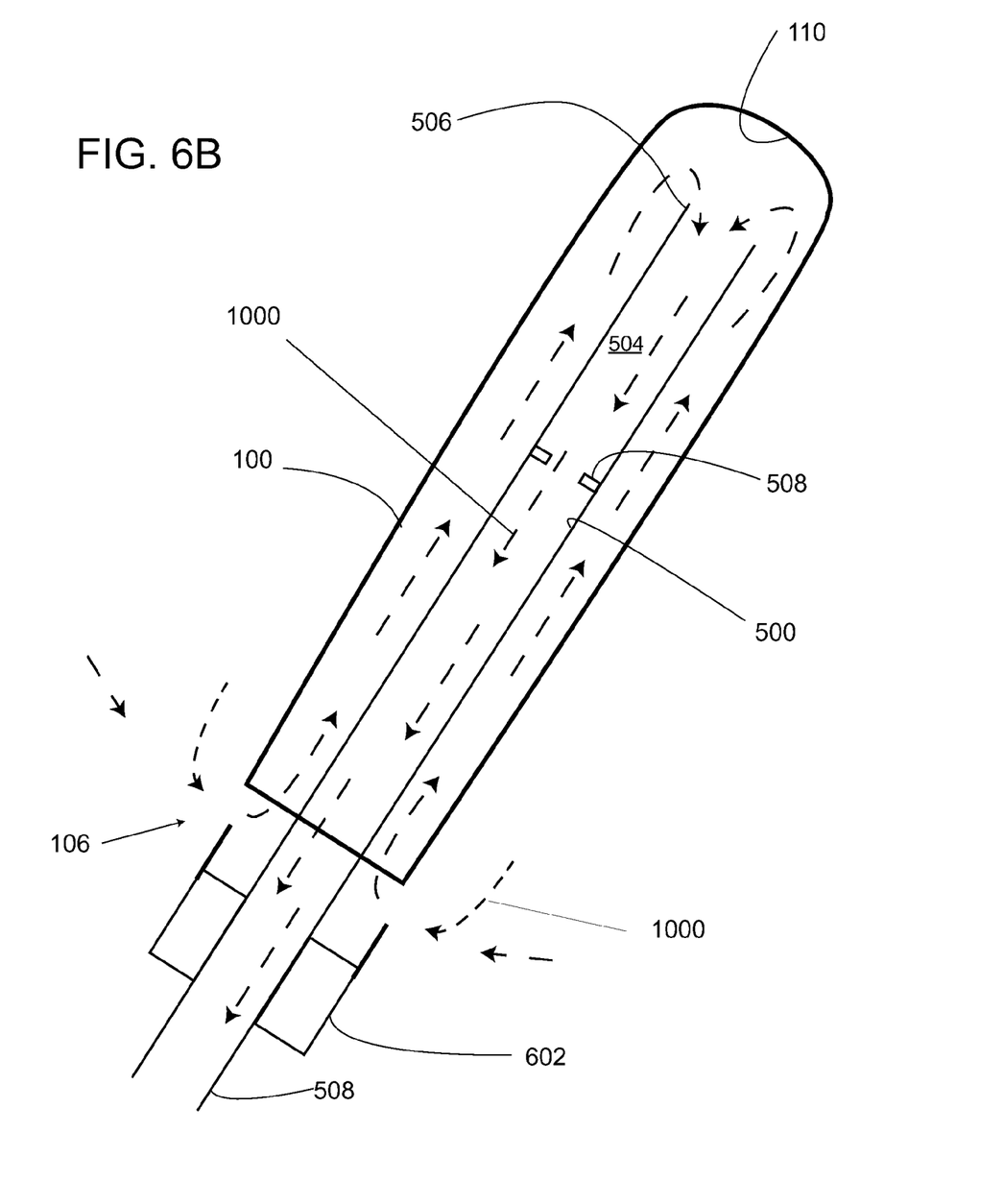
FIG. 6B shows a schematic view of a portion of the embodiment of FIG. 6A.

If one desires to replace the larger common sizes of slider-bowl, inner tubes (500) with constant outer diameters of 15 or 16 mm may be used but it would be necessary to alter the diameter of the outer tube (100) given in the example above accordingly so as to make the outer tube (100) large enough to accommodate a larger 15 or 16 mm outer diameter inner tube (500) with adequate space for appropriate air flow. Alternatively, an inner tube (500) may be constructed such that only the proximal section of the inner tube (500) has an outer diameter appropriate to fit the chosen size of slider-bowl receiving tube (608). The more distal portion of the inner tube (500) may be wider or narrower as desired. FIG. 6B is a schematic drawing of the slider-bowl version seen in FIG. 6A. The airflow is more clearly presented in this figure.

Figure 7:
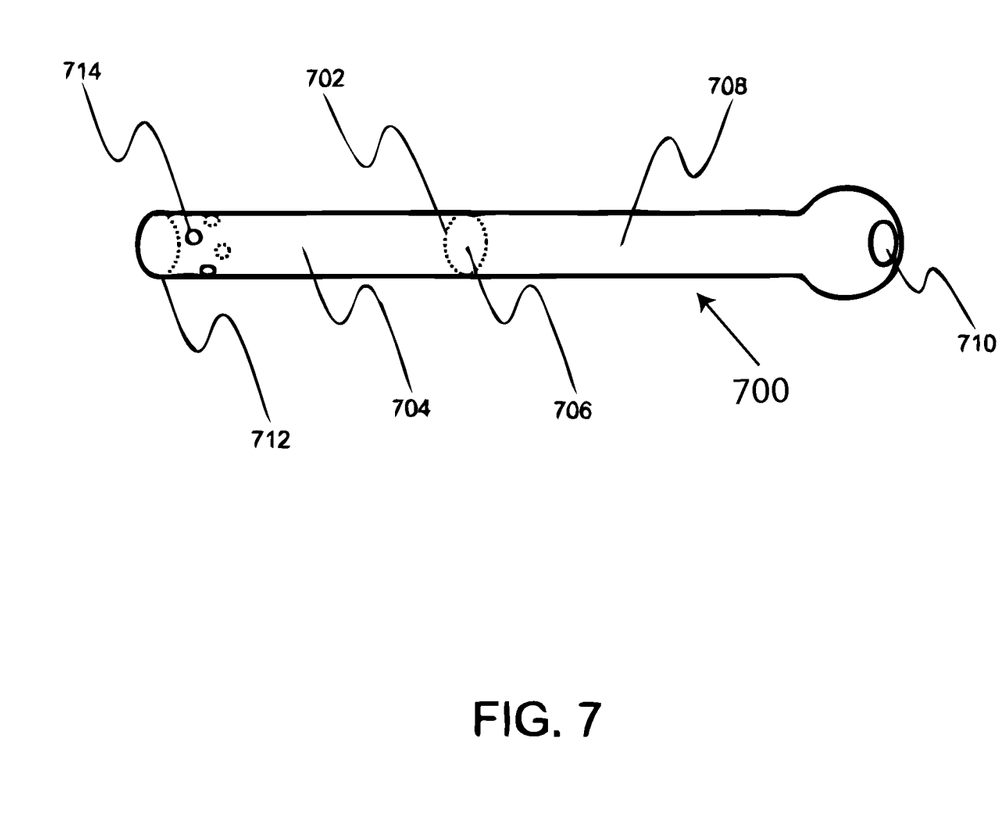
FIG. 7 shows an example of an inner vessel for a cigarette-holder embodiment.

Referring to FIG. 7, an example of an inner tube (700) for the 'cigarette holder embodiment' is shown. The outer tube (100) used for this example is substantially the same as that used for the 'portable vaporizer embodiment' (400) above. The example of the 'cigarette holder embodiment,' differs from the 'portable vaporizer' example above (400) in that the partition (702) in the inner tube (700) is placed at 9.5 cm from the distal end of the inner tube (700). The vaporization chamber (704) is thus large enough to accommodate a standard cigarette. The dimensions can be adjusted to accommodate other cigarette sizes.

Further, this partition (702), rather than having five 1.5 mm diameter screening holes (206) through it, now has just one screening hole (706), 5 mm in diameter, through its center. This screening hole (706) is small enough to prevent a cigarette from sliding through but large enough to allow vapors from the vaporizing cigarette to pass from the vaporization chamber (704) through the partition (702) into the drawing chamber (708) and onward to the proximal end (710) of the inner tube for inhalation.

The distal end (712) of the inner tube is not crimped as in the 'portable vaporizer embodiment' (400) but rather, there are four air inlet openings (714) made through the surface of the inner tube (700), 1.5 mm in diameter each, placed equidistantly around the circumference of the inner tube (700), centered at a distance of 4.5 mm from the distal end of the inner tube (712), to allow airflow into the vaporization chamber (704). The measurements given above are typical. Generally, useful ranges for measurements for outer vessels for the 'cigarette holder embodiment' are from 9 cm to 75 cm in length and diameters ranging from 5 mm to 25 cm. Generally, useful ranges for measurements for inner vessels of this embodiment are from 9 cm to 75 cm in length and diameters ranging from 2 mm to 25 cm. The higher ends of these ranges as well as the extreme low ends of these ranges are probably more valuable for novelty applications as opposed to convenience, but can still yield functional devices. While these ranges are generally preferred for most uses, the device can be made in any size and the invention is not meant to be limited to any particular size or sizes.

Further, the air inlet openings may be varied in number, shape, size, and placement and the measurements specified in the example here are not meant to be a limitation as to the exact size, shape, number, and/or placement of the air inlet openings. Likewise, the partition (702) could be placed at other chosen distances along the tube (700), thus varying the size of the vaporization chamber (704) to accommodate other size cigarettes or portions thereof, e.g. extra long cigarettes or half cigarettes, etc.

In the above example of the 'cigarette holder embodiment,' the main pathway of air into the vaporization chamber (704) is through the air inlet openings (714) rather than around the distal end of the inner tube (712) between the distal end of the inner tube (712) and the inner surface of the distal end of the outer tube (110). The air inlet openings (714) have been added in this embodiment to ensure adequate airflow into the vaporization chamber (704) because the round distal end of the inner tube (712), may substantially seal against the round, inside surface of the distal end of the outer tube (110), thereby substantially blocking airflow around the distal end of the inner tube (712) into the vaporization chamber (704). This design allows for easy insertion of a cigarette into the distal end of the inner tube (712) where a crimped end on an inner tube (216) of this diameter would obstruct such insertion.

Other designs that allow sufficient airflow into the vaporization chamber (704) without the addition of these air inlet openings (714) are also possible. For example, the distal end of the inner tube (712) could be flared to a larger diameter and then crimped slightly, thus both allowing easy insertion of a cigarette as well as creating sufficient gaps for airflow between the distal end of the inner tube (712) and the inner surface of the distal end of the outer tube (110) when the device is assembled.

Method of Operation

In order to use the portable vaporizer, one must first load the vaporization chamber (208) at the distal end of the inner vessel (200) with vaporizable substance. To accomplish this, the inner vessel (200) and outer vessel (100) must be disassembled from one another. The vaporizable substance should be broken into small enough pieces to maximize surface area but of sufficient size pieces to minimize small particles being sucked through the screening holes (206) in the partition (204). A suitable grinding device may be employed to produce proper size pieces if desired.

One may then choose to simply insert a vaporizable substance into the vaporization chamber (208) by hand or it also works well to use the inner vessel (200) straw-like, applying suction out through the proximal end (214) to suck the vaporizable substance into the vaporization chamber (208) at the distal end.

Once the vaporization chamber (208) is filled as much as desired, holding the inner vessel (200) with vaporization chamber (208) pointed up, the inner vessel (200) with the grommet (300) thereon, should be slid fully into the outer vessel (100) so that the distal end of the inner vessel (202) abuts the inner surface of the distal end of the outer vessel (110). In this position, the grommet (300) is also in place, functioning as a removable locking one-holed stopper to close the open proximal end of the outer vessel (102). Now the assembly may be safely moved at any angle because the vaporization chamber (208) is now substantially closed off by the inner surface of the distal end of the outer vessel (110) and the vaporizable substance is therefore substantially held in place in the vaporization chamber (208).

For actual vaporization, holding the assembly (400) substantially horizontal is probably best but most degrees of tilting are acceptable so long as the distal end (104) is not tilted downward to the point where the flame heats the more proximal areas of the outer vessel (100) or where the user is endangered by having his hand, face, hair, etc over the flame. To avoid obstructing the airflow through the device (400), when holding the assembly during use, do not cover the air intake vents (106) with the hand. If an optional wrap (802) or (808) is included, hold the unit with hand only on the wrap (802) (808) in order to protect the hands from touching hot surfaces of the device (400).

To begin vaporization, hold a flame, such as that from an ordinary cigarette lighter, under the heating area (108) on the outer surface at the distal end of the outer vessel (100), such that the tip of the flame is just touching the outer vessel at the heating area located along the last 1-2 cm in length of the outer vessel (108). This specified heating area (108) is generally the optimal place to apply heat for most applications, however applying heat more proximally, so long as the device is constructed in such a manner that makes it safe to do so, may still result in successful functioning of the device, and may even be preferred in some instances.

Begin inhaling through the opening (214) in the spherical mouthpiece (212) at the proximal end of the inner vessel (200). As air is inhaled through the mouthpiece (212) in the proximal end of the assembly (400), a suction is created throughout the apparatus such that air is drawn into the device through the air intake vents (106), then flows distally between the inner (200) and outer (100) vessels, flows around the distal end of the inner vessel (202) between the distal end of the inner vessel (202) and the inner surface of the closed distal end of the outer vessel (104), then flows through the vaporizable substance contained in the vaporization chamber (208), through the screening holes (206) in the partition (204) of the inner vessel (200), then proximally through the drawing chamber (210) in the inner vessel to the hole in the mouthpiece (212) and finally, into the user's mouth and lungs.

The flame heats the glass at the heating area of the outer vessel (108), which in turn heats the air passing between the inner (200) and outer (100) vessels past this point. The heated air then heats the vaporizable substance. This is the primary heating mechanism. Secondarily, the heated glass of the outer vessel (100) and air heated by the glass of the outer vessel subsequently heat the glass of the inner vessel (200) which subsequently conducts heat to the vaporizable substance in the vaporization chamber (208). The vaporizable substance is thus heated to a suitable temperature to cause the release of desired volatile constituents.

There is a certain feel required to operate the vaporizer most effectively. When the air coming through the mouthpiece (212) starts to feel warm, vaporization is beginning. If there is any burnt taste at all, or if smoke rather than a vapor mist is produced, then the flame is being applied too intensely and should be removed momentarily. Once the unit is up to vaporizing temperature, the lighter may be removed and the unit will stay hot enough to continue vaporizing substance such that another effective inhalation may still be made. Heat and inhale until all desired volatiles are released from the substance in the vaporization chamber (208). Changes in color, taste, etc. will be indicators as to whether there is any more to be gained from continued heating of the current substance in the vaporization chamber (208). When the substance in the vaporization chamber (208) is used as much as desired, wait for the unit (400) to cool or else disassemble the unit being careful not to touch the hot distal ends of the outer (104) and inner (202) tubes. Empty the vaporization chamber (208) by dumping out or by blowing through the mouthpiece (212) and then refill for the next usage.

If any black soot gathers on the outside of the outer vessel (100) due to use of a disposable lighter, it may be wiped away with tissues or cloth. Use of a refillable butane lighter will not produce such soot and is therefore preferred.

The 'slider-bowl replacement embodiment' (600) is operated in substantially the same manner as the 'portable vaporizer embodiment' (400). First, the vaporization chamber (504) is loaded with vaporizable substance. The unit is assembled by sliding the inner vessel (500) into the outer vessel (100), such that the distal end of the inner vessel (506) abuts the inner surface of the distal end of the outer vessel (110) and such that the proximal end of the outer vessel (102) rests on the distal end of the sleeve (612) or appropriate ring, forming a seal at that juncture. The proximal end of the inner vessel (502) is slid into the slider-bowl receiving tube (608) of a water pipe (604) such that the proximal end of the sleeve (610) or appropriate ring (not pictured) abuts the mouth (606) of the slider-bowl receiving tube, forming a seal at that point. The 'slider-bowl replacement' vaporizing device (600) will make an approximately 45-degree angle with the ground depending on the particular assembly used. Then using a flame to heat the heating area (108) at the distal end of the outer vessel and drawing air through the mouthpiece of the water pipe simultaneously will produce the vaporizing effect.

In the 'cigarette holder embodiment,' an unfiltered cigarette, or portion thereof, is placed into the vaporization chamber (704) and slid until the distal end of the cigarette (or portion) is proximal to the air inlet openings (714).

REFERENCE NUMERALS IN DRAWINGS

100 Outer Vessel
102 Open proximal end of outer vessel
104 Closed distal end of outer vessel
106 Air intake vents on outer vessel
108 Heating area at distal end of outer vessel
110 Inner surface of closed distal end of outer vessel
200 Inner Vessel
202 Open distal end of inner vessel
204 Partition in inner vessel
206 Screening hole in partition in inner vessel
208 Vaporization chamber in inner vessel
210 Drawing chamber in inner vessel
212 Spherical mouthpiece at proximal end of inner vessel
214 Open proximal end of inner vessel
216 Crimp at distal end of inner vessel
218 Distal end of spherical mouthpiece of inner vessel
300 Grommet
302 Length of grommet
304 Inner diameter of grommet
306 Proximal end of grommet
308 Distal end of grommet
310 Groove
312 Rounded Lip
400 Assembled Portable Vaporizer
500 Inner vessel of 'slider-bowl replacement embodiment'
502 Open proximal end of inner vessel of 'slider-bowl replacement embodiment'
504 Vaporization chamber in inner vessel of 'slider-bowl replacement embodiment'
506 Open distal end of inner vessel of 'slider-bowl replacement embodiment'
508 Partition in inner vessel of 'slider-bowl replacement embodiment'
510 Crimp at distal end of inner vessel of 'slider-bowl replacement embodiment'
512 Screening hole in partition in inner vessel of 'slider-bowl replacement embodiment'
600 Assembled 'slider-bowl replacement embodiment'
602 Sleeve
604 Water pipe
606 Mouth of slider-bowl receiving tube of water pipe
608 Slider-bowl receiving tube of water-pipe
610 Proximal end of sleeve
612 Distal end of sleeve
700 Inner vessel for 'cigarette holder embodiment'
702 Partition in inner vessel for 'cigarette holder embodiment'
704 Vaporization chamber in inner vessel for 'cigarette holder embodiment'
706 Screening hole in partition in inner vessel for 'cigarette holder embodiment'
708 Drawing chamber in inner vessel for 'cigarette holder embodiment'
710 Open proximal end of inner vessel for 'cigarette holder embodiment'
712 Open distal end of inner vessel for 'cigarette holder embodiment'
714 Air inlet holes in inner vessel for 'cigarette holder embodiment'
800A Outer wrap on outer vessel version 1
800B Outer wrap on outer vessel version 2
802 Outer wrap version 1
804 Distal raised ridge on surface of outer vessel
806 Proximal raised ridge on surface of outer vessel
808 Outer wrap version 2
810 Vent hole in wrap
812 Distal raised ridge on surface of outer vessel
814 Heavier bead at proximal end of outer vessel
1000 Airflow path
1000' Airflow path
1003" Water line Those skilled in the art will be aware of materials, techniques and equipment suitable to produce the example embodiments presented as well as variations on the those examples. These examples are presented for purposes of illustration and description but is not intended to be exhaustive or limiting to the forms disclosed. Many modifications and variations will be apparent to those of ordinary skill in the art. The embodiments and versions help to explain the principles of the invention, the practical application, and to enable others of ordinary skill in the art to understand it. Various embodiments with various modifications as are suited to the particular application contemplated are expected.

In the following claims, the words "a" and "an" should be taken to mean "at least one" in all cases, even if the wording "at least one" appears in one or more claims explicitly. The scope of the invention is set out in the claims below.

What is claimed:

1. A device for vaporizing volatile constituents of various substances comprising:

a) an outer vessel having an inside surface, an outside surface, an open proximal end and a closed distal end; said distal end having a heating area comprised of a material that can withstand heat required to vaporize the volatile constituents;

b) an inner vessel having an inside surface, an outside surface, both open distal and proximal ends extending within the outer vessel in a concentric manner so as to leave a generally annular space between the outside surface of the inner vessel and the inside surface of the outer vessel over a majority of the length of the outer vessel; when so positioned, the inner and outer vessels together define a portion of an operative pathway for air;

c) an air intake vent only in a region at the proximate end of the outer vessel with no vent at the distal end of the outer vessel, that provides a path for ambient air to enter into the annular space between the vessels, thereby comprising the start of the operative pathway; the pathway proceeding through the annular space to an end region, the end region being closed and having a solid air-impervious surface said end region being the closed distal end of the outer vessel, and further to then proceed into the open distal end of the inner vessel and then through the inner vessel to the open proximal end of the inner vessel;

further, the air intake vent being sufficiently distant from the heating area such that fumes from a heat source providing heat to the heating area are not substantially drawn into the intake vent; and still further, within the inner vessel having a partition forming at least a partial separation of the distal portion from the proximal portion of the inner vessel, the partition suitable to positionally retain a solid material to be vaporized.

2. The device of claim 1 wherein the distance between the heating area and the air intake vent is at least about 3 inches.

3. The device of claim 1 wherein the inner vessel comprises a hollow generally cylindrical tube.

4. The device of claim 1 wherein the outer vessel comprises a hollow generally cylindrical tube.

5. The device of claim 1 wherein the inner and outer vessels each comprise a glass tube.

6. A method of volatizing and inhaling a substance comprising:

a) applying heat to a heating area at the closed, distal end of an outer tube of two concentric tubes having a space between them; the tubes comprising the device of claim 1;

b) vaporizing, by the applying of heat, of a substance in a vaporizing region in the distal portion of the inner of the two concentric tubes;

c) reducing the air pressure at the proximal end of the inner tube;

d) drawing air into an air vent effectively distant from the heating area, the drawn air proceeding to the space between the two concentric tubes towards their distal ends; further the drawn air entering an open, distal end of the inner tube, passing through the vaporizing region and through the inner tube to the inner tube's proximal end.

7. The method of claim 6 wherein the application of heat is by positioning of a flame.

8. The method of claim 6 wherein the air is hot enough to volatilize active elements of the substance but not so hot as to engender burning of the substance.

* * * * *